United States Patent [19]

Hu

[11] Patent Number: 5,586,981
[45] Date of Patent: Dec. 24, 1996

[54] TREATMENT OF CUTANEOUS VASCULAR AND PIGMENTED LESIONS

[75] Inventor: Xin-Hua Hu, 109 Squire Dr., Winterville, N.C. 28590

[73] Assignee: Xin-Hua Hu, Winterville, N.C.

[21] Appl. No.: 295,987

[22] Filed: Aug. 25, 1994

[51] Int. Cl.$^6$ .................................................. A61N 5/06
[52] U.S. Cl. ............................................................. 606/9
[58] Field of Search ................................ 606/2.5, 2, 3, 9, 606/10, 11; 128/898

[56] References Cited

U.S. PATENT DOCUMENTS

| | | |
|---|---|---|
| 4,653,495 | 3/1987 | Nanaumi . |
| 4,702,245 | 10/1987 | Schroder et al. . |
| 4,718,416 | 1/1988 | Nanaumi . |
| 4,733,660 | 3/1988 | Itzkan . |
| 4,836,203 | 6/1989 | Muller et al. . |
| 4,960,108 | 10/1990 | Reichel et al. ............................ 606/2.5 |
| 5,066,293 | 11/1991 | Furumoto . |
| 5,112,328 | 5/1992 | Taboada et al. . |
| 5,152,760 | 10/1992 | Latina . |
| 5,176,675 | 1/1993 | Watson et al. ............................ 606/2.5 |
| 5,207,671 | 5/1993 | Franken et al. . |
| 5,217,455 | 6/1993 | Tan . |

FOREIGN PATENT DOCUMENTS 9113652 9/1991 WIPO ........................................ 606/9

OTHER PUBLICATIONS

"Selective Photothermolysis: Precise Microsurgery by Selective Absoption of Pulsed Radiation", Anderson and Parrish 29 Apr. 1983 vol. 220 pp. 524–527 *Science*.

"Dynamics of Shock Waves & Cavitation Bubbles Generated by Picosecond Laser Pulses in Corneal Tissue and Water" Juhasz et al Lasers in Surg. & Medicine vol. 15 pp. 91–98(May 1994).

"Intraocular Nd:Yag Laser Surg.: Light–Tissue Interaction, Damage Range, & Reduction of Collateral Effects" A. Vogel et al IEEE Jrnl of Quantum Elec. vol. 26 No. 12 Dec. 1990.

*Primary Examiner*—Angela D. Sykes
*Assistant Examiner*—Sonya Harris-Ogugua

[57] ABSTRACT

According to the invention, a method is provided for disrupting the targeted lesion in skin, such as is necessary in treatment of vascular or pigmented lesions. A microplasma is generated in a target region of skin, the microplasma disrupting the skin ("plasma ablation") to enable removal of the targeted lesion. The microplasma absorbs radiation energy and expands, creating high pressure in the surrounding region which causes disruption of the targeted lesion in that region. A beam of pulsed laser radiation can be used to generate the microplasma by properly controlling the peak irradiance, the pulse duration and the focal spot size of the beam. The invention enables use of a laser having small pulse energy. A synchronized laser beam scan device can be used to scan the beam to provide a highly efficient system for rapid skin treatment.

17 Claims, 4 Drawing Sheets

TREATMENT OF CUTANEOUS VASCULAR AND PIGMENTED LESIONS

BACKGROUND OF THE INVENTION

1. Field of the Invention

This invention relates generally to a method for treatment of skin by disrupting the targeted lesion in the skin. In particular, the invention relates to the generation of a microplasma in the skin to effect such disruption. Most particularly, the invention relates to the use of a pulsed beam of laser radiation to generate the microplasma.

2. Related Art

In many situations it is desired to have various vascular or pigmented lesions on the human skin treated or removed. Since the introduction of the selective photothermolysis model in the early 1980s, pulsed lasers have been widely used for treatment of vascular lesions such as port-wine hemangioma, telangiectasia, venous lakes, and spider and cherry angiomas, and pigmented lesions such as tattoos (decorative and traumatic), freckles, lentigos, epidermal pigmentation, and nevus.

Selective photothermolysis is discussed in detail in R. R. Anderson et al., "Selective Photothermolysis: Precise Micro Surgery by Selective Absorption of Pulsed Radiation," *Science,* Vol. 220, pp. 524–527, 1983, the disclosure of which is incorporated by reference herein. In selective photothermolysis, thermal disruption of targeted tissue (in the case of treatment of vascular lesions or targeted pigments in the case of treatment of pigmented lesions) is accomplished by impinging laser radiation on the tissue at a wavelength such that the radiation is preferentially absorbed by the targeted tissue over surrounding (collateral) tissue within an illuminated area. The absorption of the laser radiation by various chromophores in the targeted tissue causes the targeted tissue to rapidly heat up. The rapid heating causes a pressure build-up in the targeted tissue so that the targeted tissue is ablated once the laser fluence is above a threshold value. This process is often called "thermal ablation." Thermal ablation requires the use of laser radiation at an appropriate wavelength so that the laser radiation is strongly absorbed by the targeted tissue. Damage to the collateral tissue can be reduced by using a laser pulse with a duration shorter than the thermal relaxation time of the heated target tissue in order to achieve localized heating. However, the pulse must be sufficiently long so that the targeted tissue is heated sufficiently for thermal ablation to occur.

The wavelength selectivity and pulse duration requirements of selective photothermolysis can be readily met by pulsed dye lasers. For pulsed dye lasers, the wavelength of the laser radiation is determined by the type of dye used as a gain medium, and by a wavelength tuning element (e.g., a birefringent filter, an etalon or a prism) positioned in the laser cavity. The wavelength can be tuned almost continuously in the visible range from 450 nm to 650 nm. The typical pulse duration of pulsed dye lasers ranges from less than 1 microsecond to a few hundred microseconds.

A large focal spot (which may be located on or in the human skin), i.e., a focal spot having a diameter larger than 1 millimeter, has previously been employed in pulsed laser treatments. The practice of using a large focal spot is consistent with selective photothermolysis and has the benefits of reducing surgery time (since relatively fewer spots must be irradiated for a given treatment area) and reducing scattering loss as the laser beam passes through the dermal layer of the skin. However, a large focal spot requires a large pulse energy (typically several joules) for efficient ablation of target tissue. The use of large pulse energy undesirably results in excessive collateral tissue damage. Large pulse energy also necessitates the use of a large laser system which needs to be pumped by a flashlamp. Such a laser system is costly to manufacture and maintain, has low reliability due to the short lifetime of the flashlamp, is undesirably large and has low energy efficiency.

Therefore, although the use of flashlamp pumped, pulsed dye lasers has made the treatment of vascular lesions possible without significant damage to the skin surface due to the different absorption that is smaller at skin surface than that at targeted tissue, further improvements are desirable, such as reduced collateral tissue damage (resulting in shorter recovery time of a patient after a surgical procedure), increased reliability (i.e., longer lifetime and lower internal heat generation of the pumping system), and reduced cost to manufacture and maintain the laser.

In recent years, the use of Q-switched lasers for the treatment of pigmented lesions has become more popular due to the very short (i.e., nanosecond) pulses producible with such lasers. For typical Q-switched lasers, a solid state gain medium is used to generate a pulse train, each pulse having a duration between 10 and 100 nanoseconds. The pulses are typically generated at a pulse repetition rate up to several hertz. The laser-tissue interaction resulting from nanosecond laser pulses has been believed to be governed by the selective photothermolysis model. Consequently, the principles governing the design of pulsed dye lasers have been employed in the design of Q-switched lasers for use in dermatology and plastic surgery.

However, difficulties have been encountered with this approach. Due to the small number of available solid state gain media with reasonable lasing efficiency, the wavelength adjustability of Q-switched lasers has been very limited. To disrupt various types of tissue or pigment by thermal ablation with a single laser necessitates that the laser be capable of operating at each of the different wavelengths at which the various tissues and pigments are strongly absorbing. The limited wavelength adjustability of Q-switched lasers precludes use of a single Q-switched laser for treatment of all types of tissue and pigment. Although various nonlinear optical devices can be included in a Q-switched laser system to vary the wavelength of the laser output, the complexity of these devices and the loss of pulse energy as the laser radiation passes through the device has made laser systems including such nonlinear optical devices unreliable, inefficient and expensive.

A large focal spot has also been used in previous Q-switched laser treatments. As in the case of pulsed dye lasers, this requires large pulse energy and, therefore, a flashlamp pumped, Q-switched laser system. For nanosecond laser pulses, such as are used in Q-switched laser systems, it has been shown experimentally that the collateral tissue damage in the neighboring area of the ablation site is primarily determined by the pulse energy. Therefore, the use of large focal spots when using a Q-switched laser system for dermatology and plastic surgery could give rise to large amounts of collateral tissue damage resulting from the large pulse energy.

Significant technological advances have recently been made in the design and use of diode-laser pumped, solid state lasers, including Q-switched lasers. These new solid state lasers have the advantages of high energy efficiency, superior beam quality, compact size, and low maintenance cost. For example, the energy efficiency, which is defined as the average optical output power of the laser divided by the electrical input power to the laser, of a typical flashlamp pumped, pulsed laser is approximately 0.1% or less. In contrast, the energy efficiency of a diode-laser pumped, Q-switched laser can be as high as 10%. Moreover, the lifetime of the diode-laser is approximately 20 to 30 times longer than that of the flashlamp. At the present time, however, only diode-laser pumped, Q-switched lasers with a small pulse energy (on the order of magnitude of 10 millijoules) can be manufactured at a cost less than or comparable to the flashlamp pumped lasers. For the large focal spots typically used, these low energy lasers cannot efficiently ablate tissue.

The use of Q-switched lasers with small pulse energy is desirable in order to reduce excessive collateral tissue damage (i.e., patient recovery time) and to take advantage of the recent developments in diode-laser pumping technology that have enabled production of a reliable and low cost Q-switched laser system. However, in order to use low energy Q-switched lasers, new approaches for using Q-switched lasers in the treatment of vascular and pigmented lesions in human skin, other than selective photothermolysis, have to be introduced.

SUMMARY OF THE INVENTION

A method is provided for disrupting the targeted lesion in skin, such as is necessary in treatment of vascular or pigmented lesions. The targeted lesion is the tissue of malformation in the treatment of vascular lesions and the pigment in the treatment of pigmented lesions. The method is particularly useful for treatment of the dermal skin layer without damaging the superficial skin layers (which include, for instance, the stratum corneum and the epidermal skin layer) due to the different illuminating area of a laser beam that is larger in the superficial layers than that at the targeted lesion in the dermal layer. The invention can also be used to treat the superficial skin layers.

According to the invention, a microplasma is generated in a target region of skin. The microplasma absorbs radiation energy and expands. The expanding microplasma creates high pressure in the region surrounding the microplasma so that disruption of tissue or pigment is caused in that region, thereby enabling removal of the tissue or pigment. A pulsed beam of laser radiation can be used to generate the microplasma by properly controlling the peak irradiance, the pulse duration and the focal spot size of the beam.

One embodiment of the method according to the invention includes the steps of: i) generating a pulsed beam of laser radiation; ii) directing the beam to a target region of the skin; and iii) controlling the peak irradiance, the pulse duration and the focal spot size of the beam such that a microplasma is created within the skin. An apparatus that can be used according to the invention includes a laser for generating a pulsed beam of laser radiation and structure for directing and controlling the beam as described above.

In a particular embodiment, the pulse duration is maintained between approximately 0.1 nanoseconds and approximately 100 nanoseconds. In another particular embodiment, the pulse duration is maintained between approximately 0.1 nanoseconds and approximately 50 nanoseconds. Pulses longer than the upper limit of the above-specified ranges may not produce a microplasma. Pulses shorter than the lower limit of the above-specified ranges require a more complex (and, thus, more expensive) laser system than is necessary to produce pulses having a duration in the ranges specified. Pulse durations having a magnitude according to the invention can be produced, for instance, by a Q-switched laser. Generally, the invention includes within its scope pulses having a duration that avoid the undesirable effects discussed immediately above.

In another particular embodiment, the peak irradiance is maintained between approximately $10^7$ W/cm$^2$ and approximately $10^{12}$ W/cm$^2$. Pulses having a peak irradiance in this range are effective in producing a microplasma in skin.

In yet another particular embodiment, the diameter of the focal spot is maintained between approximately 5 micrometers and approximately 500 micrometers. In a further particular embodiment, the diameter of the focal spot is maintained between approximately 10 micrometers and approximately 500 micrometers, and in a still further particular embodiment, the diameter of the focal spot is maintained between approximately 50 micrometers and approximately 500 micrometers. If the diameter of the focal spot is smaller than the lower limit of the above-specified ranges, then treatment of a given region of skin requires an undesirably long period of time. If the diameter of the focal spot is larger than the upper limit of the above-specified ranges, then a relatively large pulse energy is required, with accompanying disadvantages as discussed in more detail above. Generally, the invention includes within its scope focal spots having a size that avoids the undesirable effects discussed immediately above.

In still another particular embodiment, each of the pulse duration, the peak irradiance and the focal spot size are maintained within the above-described ranges.

Control of the pulse duration, the peak irradiance and the focal spot size as described above allows a low pulse energy laser to be used. A laser according to the invention has a pulse energy that is approximately 20 to 30 times lower than the pulse energy of previously used lasers. Preferably, the pulse energy of the laser is between approximately 0.1 millijoules and approximately 100 millijoules. The use of a low pulse energy laser reduces collateral tissue damage and allows use of low cost diode-laser pumped lasers with their accompanying advantages, i.e., high energy efficiency, superior beam quality, compact size, low maintenance cost and high reliability. Generally, the invention includes within its scope lasers having a pulse energy that provides the benefits discussed immediately above.

If thermal ablation is believed to be responsible for tissue disruption, the limited wavelength adjustability of Q-switched lasers precludes use of a single Q-switched laser for treatment of all types of tissue and pigment. The absorption of laser energy by microplasma to cause disruption of the targeted lesion is relatively insensitive to the wavelength of the laser radiation, so that, according to the invention, a single Q-switched laser can be used to treat all types of tissues and pigments. Also, the wavelength of laser radiation for use with the invention is chosen to minimize loss of laser pulse energy as the laser radiation passes through the epidermal and dermal layers during surgery, i.e., to maximize penetration depth of the laser beam. In one embodiment of the invention, the wavelength of each pulse of laser radiation is between approximately 800 nanometers and approximately 1400 nanometers.

In another embodiment of the method according to the invention, the method includes the additional step of applying pressure to the target region of the skin. This pressure helps to reduce the scattering loss of the beam in the dermal tissue anterior to the targeted lesion in the skin and so is particularly useful in treating dermal lesions.

The cone angle of the laser beam can also be controlled to produce beneficial effects in cutaneous treatments. In one embodiment of the invention, the cone angle of the beam has a value between approximately 5 degrees and approximately 40 degrees. In another embodiment, the cone angle has a value greater than or equal to approximately 10 degrees. A cone angle of greater than approximately 10 degrees is particularly useful to minimize unwanted tissue ablation in tissue that is anterior to the target region of the skin. Generally, the invention includes within its scope laser beams having a cone angle that minimizes such unwanted tissue ablation.

According to one embodiment of the invention, the laser is a Q-switched laser. In a further embodiment, the Q-switched laser includes a gain medium that is a Nd:YAG crystal. In another further embodiment, the Q-switched laser includes a gain medium that is a Nd:YLF crystal. In still another further embodiment, the Q-switched laser includes a gain medium that is a $Nd^{3+}$ doped material.

In another embodiment according to the invention, an apparatus for treating skin includes a laser for generating a pulsed beam of laser radiation, a scanning device for automatically directing the laser beam to each of a plurality of locations within a treatment area of the skin, and a focusing mechanism for controlling a focal spot size of the laser beam so that the focal spot size is approximately the same at each of the locations. In a particular embodiment, the diameter of the focal spot is maintained in a range as specified above.

In yet another embodiment according to the invention, an apparatus for treating skin includes a laser for generating a pulsed beam of laser radiation and a scanning device for automatically directing the laser beam to each of a plurality of locations within a treatment area of the skin such that exactly one radiation pulse is delivered to each location. In one particular embodiment, the pulse repetition rate of the pulses is between approximately 10 Hz and approximately 10 kHz, and in a further particular embodiment, the pulse repetition rate is between approximately 10 Hz and approximately 1000 Hz. Because only one radiation pulse is delivered to each location, ablation efficiency is increased since the scattering of subsequent laser pulses by an existing gas bubble inside the skin tissue, created by the first laser pulse, is avoided. Further, scanning of the laser pulse decreases the amount of time required to treat a given region of skin.

DETAILED DESCRIPTION OF EMBODIMENTS OF THE INVENTION

According to the invention, microplasma is generated in a target region of skin, the microplasma disrupting the skin ("plasma ablation") to enable removal of the targeted lesion in the treatment of vascular and pigmented lesions, as well as other skin disorders. A pulsed beam of laser radiation can be used to generate the microplasma by properly controlling the peak irradiance (peak power per unit area irradiated), the pulse duration and the focal spot size of the beam.

As shown by equation (1), peak irradiance $I_p$ is a function of the pulse energy $E_p$, the pulse duration $t_p$, and the area of the illuminated spot ("spot size") $A_f$ of the radiation pulses. The peak irradiance $I_p$ varies directly with the pulse energy $E_p$ and inversely with the pulse duration $t_p$ and the spot size $A_f$.

$$I_p = E_p/(t_p * A_f) \quad (1)$$

As the peak irradiance is increased, a strong transient electric field is created in the focal region of the laser radiation, the focal region being on the surface of, or within, the skin. When the electric field strength reaches a threshold level, optical breakdown begins, generating a plasma of ionized particles in a highly localized region ("microplasma"). The microplasma absorbs the laser radiation and expands, creating high pressure in the surrounding region which causes disruption of the the targeted lesion in that region. According to one embodiment of the invention, to achieve plasma ablation in skin, the peak irradiance of the radiation pulses is increased to be between approximately $10^7$ W/cm$^2$ and approximately $10^{12}$ W/cm$^2$. In a different embodiment, the peak irradiance is maintained between approximately $10^8$ W/cm$^2$ and approximately $10^{11}$ W/cm$^2$.

Notwithstanding the magnitude of the peak irradiance, in order for a microplasma to be generated, the pulse duration of the radiation pulses must be properly controlled. Generally, decreasing the pulse duration enhances the ability to generate a microplasma. As is best understood, the less time it takes for electrons to absorb a certain amount of radiation energy (i.e., the shorter the rise time for the irradiance of a laser pulse to reach its peak level), the smaller the probability that excited electrons will de-excite themselves by transferring energy to ions, atoms and molecules in the irradiated tissue. Consequently, shortening the pulse duration makes it easier to accumulate the large number of highly excited electrons necessary for the onset of optical breakdown. According to the invention, in one embodiment, the pulse duration is kept between approximately 0.1 nanoseconds and approximately 100 nanoseconds. In another embodiment, the pulse duration is kept between 0.1 and 50 nanoseconds. If the pulse duration is longer than approximately 100 nanoseconds, it is believed that a microplasma may not be generated and mechanisms other than plasma ablation may dominate the ablation process. To produce a pulse duration shorter than approximately 0.1 nanoseconds, it is often necessary to use a more complex (and, thus, more expensive) laser system (e.g., two lasers, rather than one, may be required) than is necessary to produce pulse durations in the ranges specified.

Additionally, to reduce collateral tissue damage, the focal spot size must be properly controlled. According to the invention, in one embodiment, the diameter of the focal spot is controlled to be between approximately 5 micrometers and approximately 500 micrometers. In other embodiments, the diameter of the focal spot is controlled to be between approximately 10 micrometers and approximately 500 micrometers, or between approximately 50 micrometers and approximately 500 micrometers. If the diameter of the focal spot is larger than approximately 500 micrometers, it is believed that excessive collateral tissue damage may be unavoidable due to the large pulse energy necessary for efficient ablation. On the other hand, if the diameter of the focal spot is less than approximately 5 micrometers, treatment of a given region of skin requires too much time.

Control of the peak irradiance, the pulse duration and the spot size as described above enables a low pulse energy, i.e., between approximately 0.1 millijoules and approximately 100 millijoules, to be used. Consequently, disruption of the targeted lesion is highly localized and damage to collateral tissue or pigment resulting from thermal diffusion is minimized. Additionally, use of flashlamp pumped lasers, with their attendant disadvantages (as described in more detail above), can be avoided.

Figure 1:
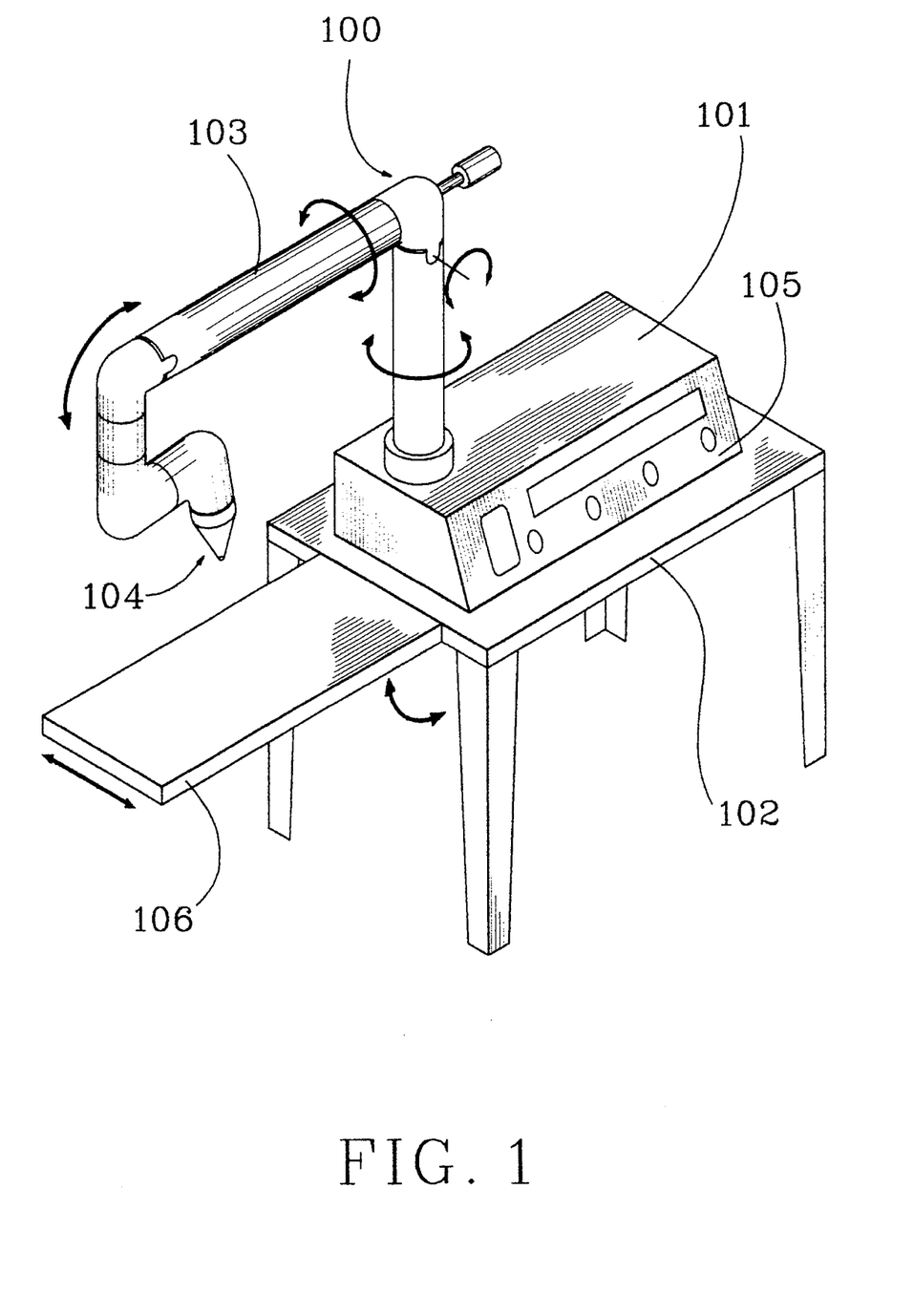
FIG. 1 is a simplified perspective view of a laser treatment apparatus according to the invention.

FIG. 1 is a simplified perspective view of a laser treatment apparatus 100 according to the invention. A laser system (see FIG. 2) is enclosed within a housing 101 that is mounted on a table 102. A control panel 105 on the housing 101 is used to control the laser system to produce radiation that is directed out of the housing 101, guided through an articulated arm 103, and emitted from a contact head 104. The portion of the patient's body to be treated rests on a shelf 106, which can be moved laterally with respect to the table 102, as indicated by the directional arrow. The shelf 106 can also be rotated out of the way against the legs of the table 102, as indicated by the directional arrow. The laser radiation emitted from the contact head 104 impinges upon the skin to be treated. The articulated arm 103, shown in simplified form in FIG. 1 and described in more detail below with respect to FIG. 3, includes several sections, each of which can be rotated about its own axis or with respect to an adjacent section, as indicated by the directional arrows, so that the contact head 104 can be moved to any desired position and the laser radiation can be emitted from the contact head 104 in any desired direction.

Figure 2:
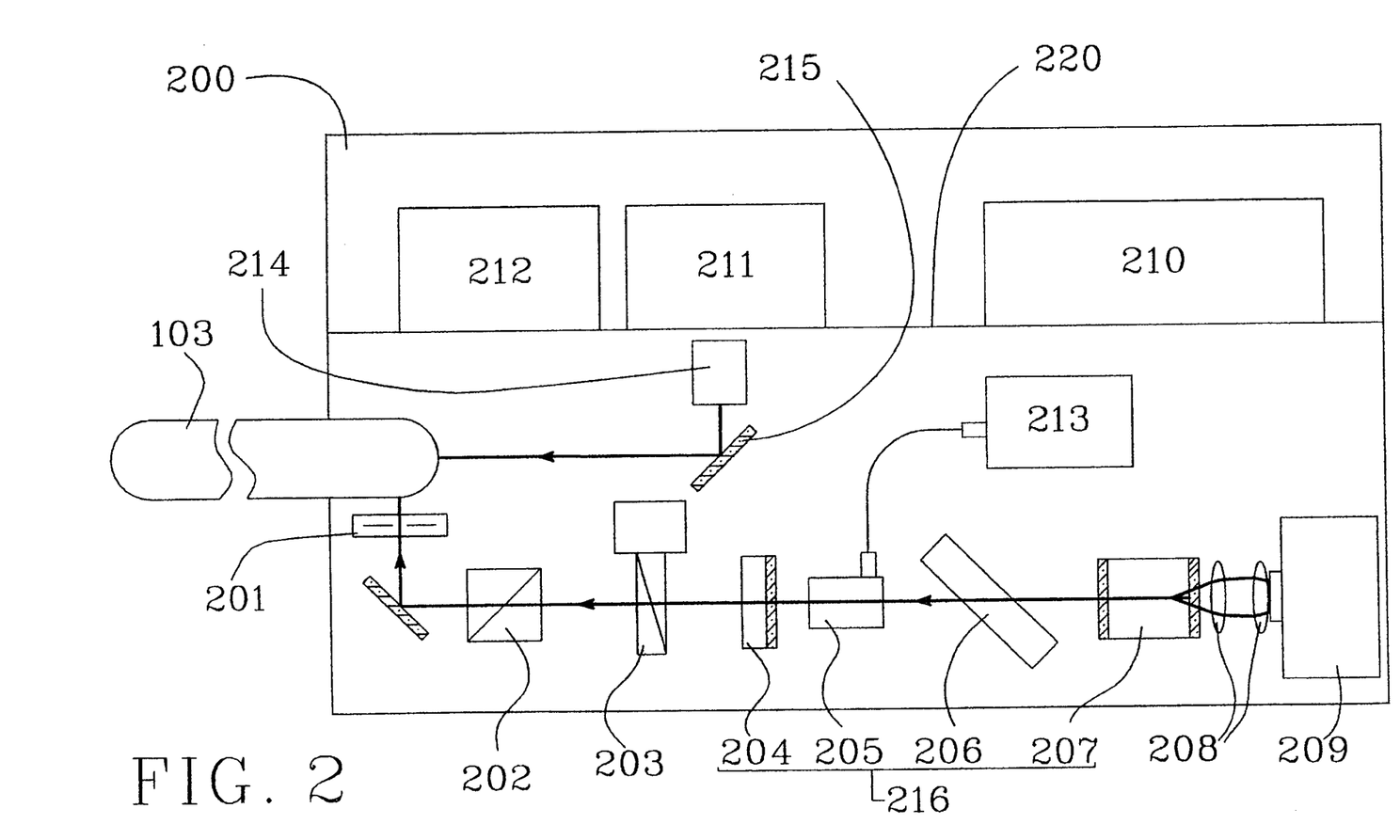
FIG. 2 is a top view of the laser treatment apparatus of FIG. 1 with the upper surface of the housing removed, showing a simplified representation of a laser system according to the invention within the housing.

FIG. 2 is a top view of the laser treatment apparatus 100 with the upper surface of the housing 101 removed, showing a simplified representation of a laser system 200 according to the invention within the housing 101. FIG. 2 diagrammatically illustrates the components of the laser treatment apparatus 100 within the housing 101. The components 210, 211 and 212 are positioned on a lower shelf within the housing 101, and the components 201 through 209 and 213 through 215 are positioned on an upper shelf, the different positioning being indicated by the line 220 separating the two groups of components. Components 204 through 209, discussed in more detail below, together constitute a standard diode-laser pumped, Q-switched solid state laser in an end pumping configuration. The Q-switched laser includes components 204 through 207 and is designated collectively as element 216 in FIG. 2.

A diode-laser head 209 produces laser radiation which is collimated and focused into a gain medium 207 by coupling optics 208. The gain medium 207 is a solid-state material. In one embodiment, the gain medium 207 is a Nd:YAG crystal. In another embodiment, the gain medium 207 is a Nd:YLF crystal. In another embodiment, the gain medium 207 is a $Nd^{3+}$ doped material. The laser radiation from the diode-laser head 209 excites the crystals of the gain medium 207. The excited gain medium 207 emits light as the crystals return to the ground state.

A laser cavity is defined by one end surface of the gain medium 207 and a partial reflecting output coupler 204. The Q-switch is located within the laser cavity and pulses the laser radiation. In one embodiment, the Q-switch consists of a polarizer 206 and an electro-optical crystal 205 (a power supply 213 supplies power to the electro-optical crystal). In another embodiment, the Q-switch is an acousto-optic modulator. In yet another embodiment, the Q-switch is a saturably absorbing material, the material having an appropriate thickness given the optical properties of the material, as known by those skilled in the art. In a particular embodiment, the Q-switch pulses the laser beam so that the pulse repetition rate is between 10 Hz and 10 kHz. In another particular embodiment, the pulse repetition rate is between 10 and 1000 Hz.

The end surface of the gain medium 207 facing the partial reflecting output coupler 204 is coated with an antireflection coating that nominally permits full passage of radiation at the wavelength of the laser radiation emitted from the gain medium 207. The end surface of the gain medium 207 facing the diode-laser head 209 has one coating with a nominal 100% reflection of radiation at the wavelength of the laser radiation emitted from the gain medium 207, and another, antireflection coating that nominally permits full passage of radiation at the wavelength of the laser radiation emitted from the diode-laser head 209.

Preferably, the wavelength of laser radiation emitted from the gain medium 207 (i.e., from the Q-switched laser 216) is between 800 and 1400 nanometers. The choice of laser radiation having a wavelength between 800 and 1400 nanometers (near-infrared laser beam) reduces the loss of pulse energy due to absorption and scattering by the skin tissue as the laser beam passes through various layers of the skin. The wavelength of laser radiation emitted from the diode-laser head 209 is typically somewhat shorter than that emitted from the Q-switched laser 216, e.g., between 600 and 1200 nanometers.

The energy of each radiation pulse is controlled by a energy modulation system that includes a rotatable waveplate 203 and a polarizer 202. The pulsed laser radiation is turned on or off with an electronically controlled (e.g., foot switch) mechanical shutter 201.

As apparent from the discussion above, the wavelength of the radiation produced by the Q-switched laser 216 is in the near-infrared range of the spectrum. To aid the alignment of the invisible near-infrared laser beam on the skin of the patient, a dual-beam (red, in one embodiment) produced from a small power, visible light laser 214 (such as a He-Ne laser) with a beam splitter 215 is sent coaxially with the near-infrared beam into the articulated arm 103.

The housing 101 also encloses a power supply 210, control boards 211 and a scanner control board 212 for enabling the operation of the laser treatment apparatus 100 as described above and below.

Each of the components 201 through 215 are conventional and are commercially available from a variety of sources.

As noted above, the generation of microplasma in the skin requires the presence of a strong transient electric field. As also noted above, a sufficiently strong field can be produced with a low pulse energy laser if the radiation pulses have a short pulse duration (e.g., 0.1 to 100 nanoseconds) and have a small spot size (e.g., a focal spot diameter of 5 to 500 micrometers).

All other things being equal, the treatment of a given skin area with a small focal spot would take longer than treatment of the same area with a large focal spot. Such prolonged surgery may be unacceptable. To overcome this potential problem, according to the invention, the near-infrared laser beam is pulsed at a high pulse repetition rate (e.g., 10 Hz to 10 kHz) and scanned over a treatment area by a computerized fast scanning device, as described in more detail below, at a speed such that only one laser pulse is delivered to any given location in the treatment area and the entire treatment area is treated in a time that is comparable to that of previous treatments using large focal spots.

Typically, previous laser treatment systems using a beam with large focal spot size have not included a beam scanning device. Instead, the beam is moved over the treatment area manually by a surgeon using a handpiece at the end of an articulated arm. Since this manual movement is typically rather slow, often, multiple laser pulses are applied to a given location, in contrast to the laser treatment apparatus 100 in which only a single pulse is applied to any given location. Ablation efficiency (defined here as mass of the disrupted lesion per unit of energy deposited) is higher for one pulse per location than for multiple pulses per location, since the scattering of subsequent laser pulses by an existing gas bubble inside the skin tissue, created by the first laser pulse, is avoided.

Figure 3:
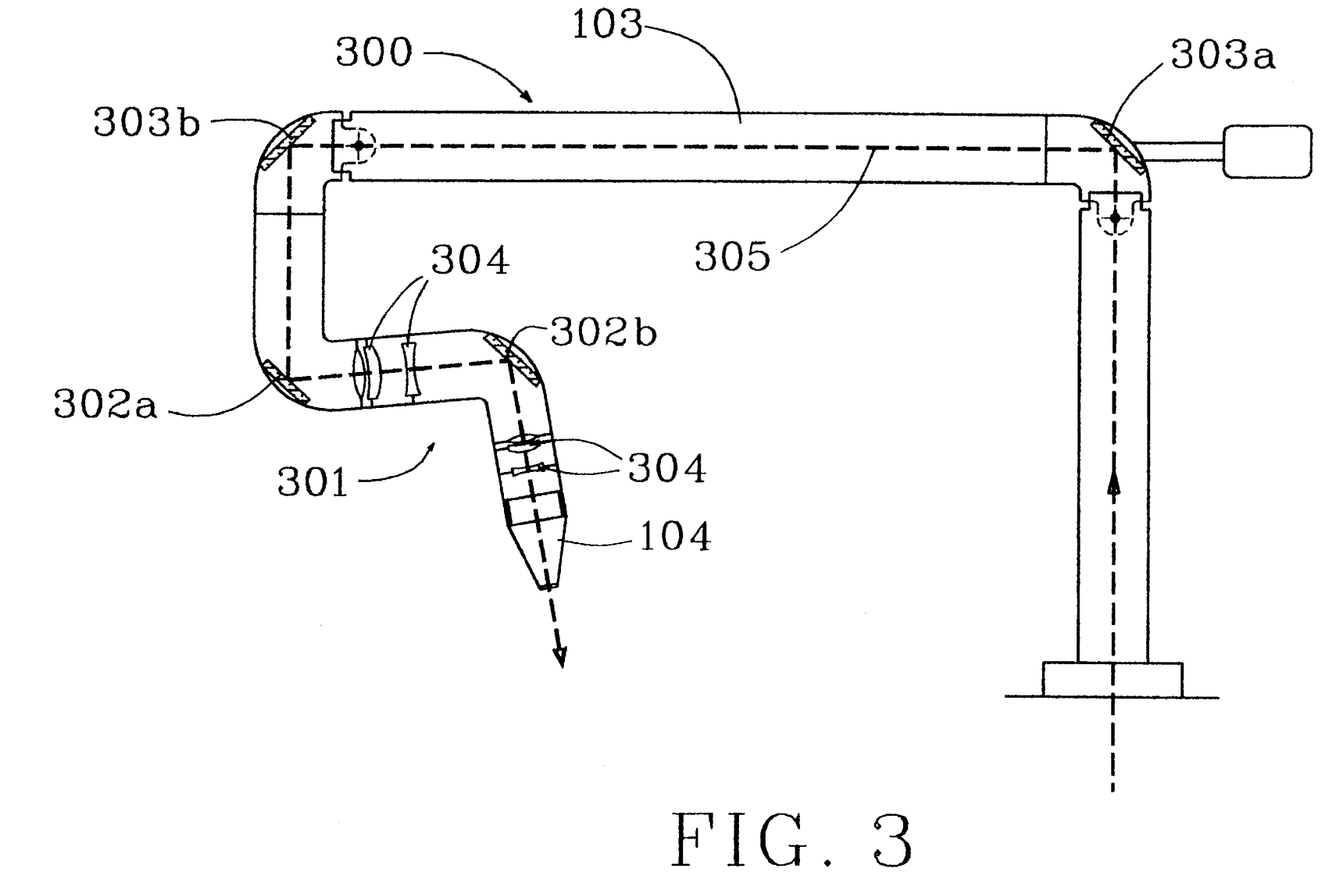
FIG. 3 is a cross-sectional view of an optical delivery mechanism according to the invention for use with the laser treatment apparatus of FIG. 1.

In order to achieve the above benefits, the laser treatment apparatus 100 must be able to generate a high repetition rate nanosecond pulse train and must include an optical delivery mechanism that is capable of strongly converging and scanning the near-infrared laser beam synchronously with the pulse repetition rate. FIG. 3 is a cross-sectional view of an optical delivery mechanism 300 according to the invention for use with the laser treatment apparatus 100. The optical delivery mechanism 300 includes three main components: i) the articulated arm 103; ii) a handpiece 301 which includes motorized mirrors 302a and 302b, and a combination of lenses 304 (six are shown for illustrative purposes in FIG. 3; however, generally, more lenses are used); and iii) the contact head 104 which includes a contact piece (see FIG. 4). The near-infrared laser beam and dual-beam are directed along an optical path 305 in the optical delivery mechanism 300 by the mirrors 303a and 303b located at bends in the articulated arm 103, and by the motorized mirrors 302a and 302b of the handpiece 301.

The function of the articulated arm 103 is to provide three dimensional freedom of movement of the handpiece 301 while the remainder of the laser treatment apparatus 100 remains stationary. The articulated arm 103 is constructed using techniques known to those skilled in the art of construction of such devices. As a consequence of the construction of the articulated arm 103, the near-infrared laser beam can be emitted from the contact head 104 in any desired direction.

The handpiece 301 includes the scanning device discussed above. Generally, the scanning device includes a group of mirrors. In one embodiment, shown in FIG. 3, the scanning device includes two mirrors 302a and 302b (though more or less could be used) so that the near-infrared laser beam can be scanned in any predetermined two-dimensional pattern. If more mirrors are used, the near-infrared laser beam can be scanned over a three-dimensional region in space. Each of the mirrors, e.g., mirrors 302a and 302b, is assembled on the shaft of a galvanometer (not shown in FIG. 3). Each shaft can be accurately rotated through a small angle and is controlled by an electronic signal provided by a computer or microprocessor, e.g., scanner control board 212 (FIG. 2). The mirrors and the associated galvanometers are commercially available from a variety of sources. By using a scanning device and synchronizing the scanning device control signal with the high repetition rate laser pulse, a large area per second can be efficiently treated with a very small focal spot.

The handpiece 301 also includes the lenses 304 (which, in practice, typically number approximately 15 or less). The lenses 304 focus the near-infrared laser beam to have a predetermined spot size at a specified cone angle, and ensure that these focusing parameters remain the same as the near-infrared laser beam is scanned. The specific arrangement of the lenses 304 can be implemented by one skilled in the art of optics.

The contact head 104 includes a contact piece (described in more detail below with respect to FIG. 4) that contacts the skin during treatment. The contact head 104 is adjustable with respect to the handpiece 301. The distance between the focal spot and the lens (also called the objective lens) within the handpiece 301 that is closest to the contact head 104 is constant. However, the distance between the objective lens and the external surface of the contact piece 406 can be changed, through adjustment of the contact head 104, so that the focal spot can be placed at a variable distance from the external surface of the contact piece 406. The movement of the contact head 104 is limited so that the focal spot of the near-infrared laser beam 407 is always outside of the contact head 104.

Figure 4:
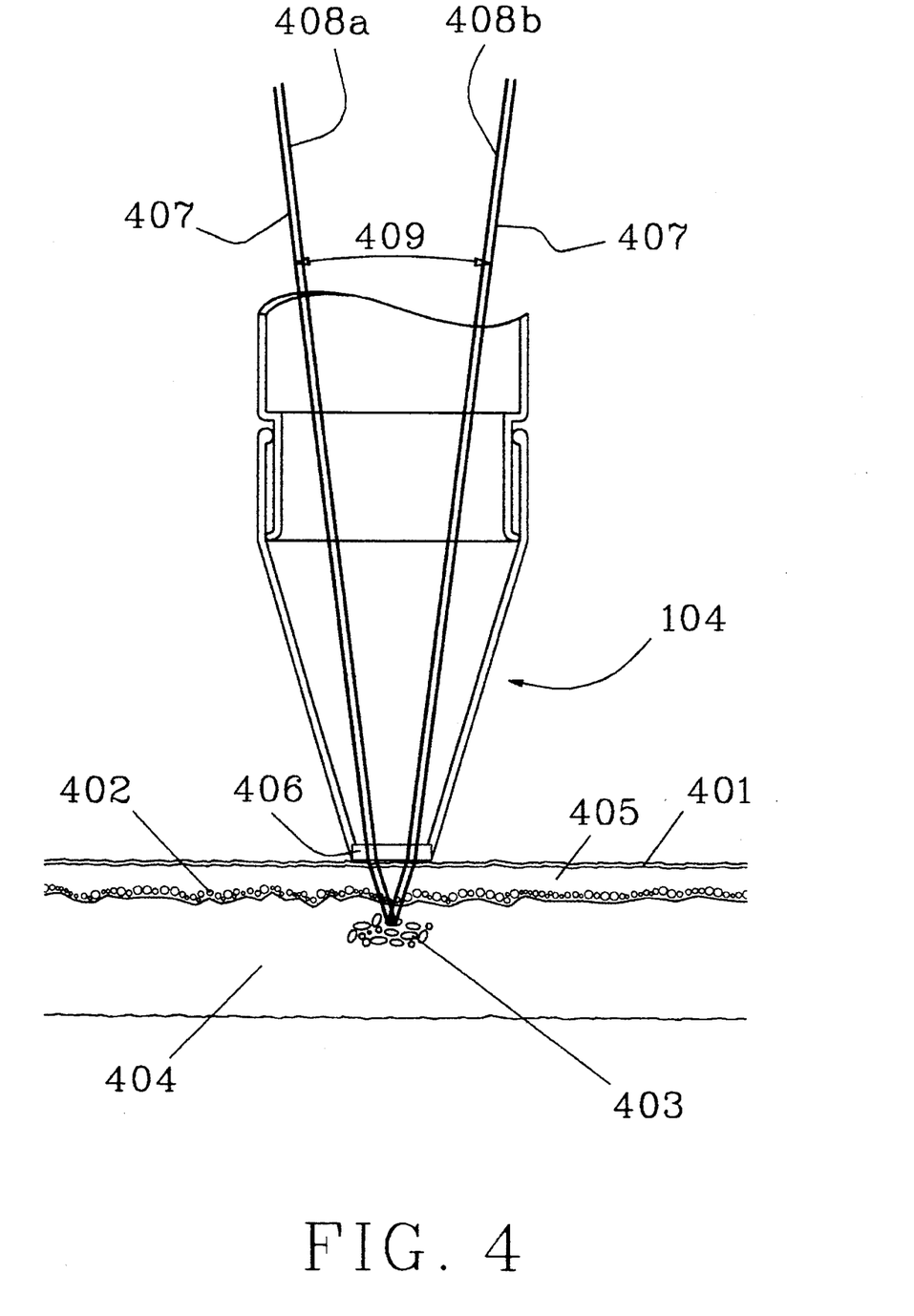
FIG. 4 is a cross-sectional view of a portion of the contact head of the optical delivery mechanism of FIG. 3 with a contact piece of the contact head in contact with an outer layer of a patient's skin.

FIG. 4 is a cross-sectional view of a portion of the contact head 104 of the optical delivery mechanism 300 with the contact piece 406 in contact with a stratum corneum 401 of a patient's skin. The near-infrared laser beam 407 from the Q-switched laser 216 and the beams 408a and 408b from the dual-beam laser 214 are shown entering the patient's skin. The near-infrared laser beam 407 is shown in FIG. 4 by two lines defining the outline of the near-infrared laser beam 407. Each of the beams 408a and 408b is shown in FIG. 4 as a single line.

The contact piece 406 includes a flat window made of transparent material, such as quartz, and is assembled at an end of the contact head 104 distal from the handpiece 301 (FIG. 3). For surgical treatment in the superficial layers of a patient's skin (the superficial layers include skin that can be seen from the surface of the skin), the contact piece 406 including a flat window can be replaced with a contact piece not having a window, so that damage to the window can be avoided.

The contact piece 406 serves two purposes when in contact with the patient's skin. First, for a given position of the contact head 104 with respect to the handpiece 301, the contact piece 406 places the focal spot of the near-infrared laser beam 407 at a particular depth with respect to the skin surface. The laser treatment apparatus 100 can focus pulsed laser radiation on target in the epidermal layer 405 in the treatment of surface disorder, or in the dermal layer 404 in the treatment of dermal disorder. Second, the contact piece 406 can be used to apply some pressure to the skin in order to reduce the scattering loss of the near-infrared laser beam 407 in the dermal layer 404 in the treatment of dermal disorders. These features are particularly useful in treating dermal disorder under the epidermal layer 405.

In an alternative embodiment, the optical delivery mechanism 300 includes only the contact head 104 and the handpiece 301 if the laser beam generating portions (i.e., components 201 through 209 and components 213, 214 and 215) of the laser system 200 are small and light enough to be moved around by hand. In this embodiment, the laser beam generating portions of the laser system 200 are preferably made very compact and can be separated from the other parts of the laser system 200, such as the power supply 210. In this embodiment, during surgery, the surgeon is able to hold by hand the laser beam generating portions of the laser system 200 and the optical delivery mechanism 300.

The near-infrared laser beam 407 from the Q-switched laser 216 (FIG. 2) and the beams 408a and 408b from the small power, visible light, dual-beam laser 214 are directed through the articulated arm 103 and out of the contact piece 406 into the patient's skin. The near-infrared laser beam 407 is focused by the objective lens, and the contact head 104 is positioned relative to the handpiece 301, so that the focal spot of the near-infrared laser beam 407 is in the vicinity of the targeted lesion 403 in the dermal layer 404. The angle between the beams 408a and 408b is the same as the cone angle 409 of the near-infrared laser beam 407 so that the beams 408a and 408b converge at the focal spot of the near-infrared laser beam 407. The convergence of the visible light beams 408a and 408b is used to identify the location of the focal spot of the invisible near-infrared laser beam 407. The objective lens is preferably constructed so that the cone angle 409 of the near-infrared laser beam 407, and the angle between the dual beams 408a and 408b, has a magnitude between 5 and 40 degrees. A cone angle of greater than 10 degrees is particularly useful to minimize unwanted tissue ablation in the epidermal layer 405, the dermal layer 404 and the epidermal-dermal junction 402 which are anterior to the targeted lesion 403.

As noted above, the laser beams 408a, 408b and 407 are scanned automatically over a treatment area, the size of which is defined by the size of the surface of the contact piece 406 that contacts the patient's skin. The scanned treatment area, which can be, for example, circular or rectangular, has a primary dimension (i.e., diameter for circular treatment area and length of side for rectangular treatment area) from 1 to 20 millimeters depending on the size of the contact piece 406. After completion of the treatment of the treatment area, the handpiece 301 is successively manually moved to other locations and treated with the near-infrared laser beam 407 until treatment of a desired region of the patient's skin is completed. By scanning the near-infrared laser beam 407 at a high pulse repetition rate, e.g., between 10 Hz and 10 kHz, the treatment time can be decreased significantly for the small spot size according to the invention, e.g., a focal spot diameter between approximately 5 micrometers and approximately 500 micrometers.

As discussed above, the peak irradiance of the pulsed laser radiation must be increased above a threshold value to generate a plasma for plasma ablation. In contrast to thermal ablation, in microplasma ablation the absorption of laser radiation by the the targeted lesion only influences the threshold peak irradiance necessary for generation of the microplasma; the laser radiation absorption by the the targeted lesion does not directly result in disruption of the the targeted lesion. Once the threshold is reached, the generated microplasma absorbs the laser radiation directly and expands to cause disruption of targeted lesion. While the dependence of the peak irradiance threshold on the amount of laser radiation absorption by the targeted lesion is not clearly understood, certain experimental results indicate that this dependence is weak. It has been experimentally confirmed that microplasma can be generated even in tissue which does not absorb laser radiation substantially. Therefore, according to the invention, in plasma ablation, the optimum wavelength of the laser radiation is determined according to the criterion of minimization of loss of laser pulse energy as the laser radiation passes through the epidermal and dermal layers during surgery. In contrast, in thermal ablation, the wavelength is selected to obtain the maximum absorption of laser radiation by the target tissue or pigment and the wavelength of the radiation is preferably in the visible range, e.g., red light from ruby and alexandrite lasers, or yellow light from dye and copper vapor lasers. Since such absorption is not critical in plasma ablation, near-infrared wavelength laser radiation can be used with the method of the invention.

The TABLE below gives a comparison between various parameters and characteristics of a typical prior art Q-switched laser and a Q-switched laser according to one embodiment of the invention. In the TABLE, the focal spot is assumed to be circular, the wavelength of laser radiation is equal to 1064 nanometers and the pulse duration is 10 nanoseconds.

TABLE

|  | Previous Q-switched laser | Laser according to invention |
| --- | --- | --- |
| Focal spot diameter | 2 mm | 0.1 mm |
| Maximum pulse energy required for efficient treatment | 300 mJ | 10 mJ |
| Maximum laser fluence | 300 mJ/($\pi \times 1^2$ mm) ≈ 10 J/cm$^2$ | 10 mJ/($\pi \times 0.05^2$ mm) ≈ 127 J/cm$^2$ |
| Electric field strength (in air) | 0.87 MV/cm | 3.1 MV/cm |
| Laser pumping mechanism (life time) | flash lamp (less than 400 hours) | diode laser (more than 4000 hours) |
| Typical pulse repetition rate (maximum) | 1 Hz (10 Hz) | 250 Hz (10,000 Hz) |
| Scanning device | no | yes |
| Treatment area per second | 3.1 mm$^2$ | 3.1 mm$^2$ |
| Number of spots per treatment area | 1 | 250 |
| Number of pulses per spot (maximum) | 1 (10) | 1 (1) |
| Cone angle of focusing | less than 5° | greater than 10° |
| Collateral tissue damage (smaller for smaller pulse energy/larger cone angle) | large | small |
| System power consumption | larger than 1000 W | smaller than 150 W |
| Manufacturing cost | about the same at present time (the cost of diode laser decreases continuously) | |

Various embodiments of the invention have been described. The descriptions are intended to be illustrative, not limitative. Thus, it will be apparent to one skilled in the art that certain modifications may be made to the invention as described without departing from the scope of the claims set out below.

I claim:

1. A method for treatment of cutaneous vascular and pigmented lesions, comprising the steps of:
    generating a pulsed beam of laser radiation;
    directing the beam to a target region of the skin;
    controlling the peak irradiance, the pulse duration and the focal spot size of the beam such that a microplasma is created in the targeted lesion for disruption; and
    scanning the beam within a treatment area of the skin.

2. A method as in claim 1, wherein the targeted lesion further comprises the lesion in the skin layers anterior to the skin dermis in the treatment of surface disorders and the lesion in the skin dermis in the treatment of disorders within the skin.

3. A method as in claim 1, wherein the targeted lesion further comprises the tissue of malformation in the treatment of vascular lesions and the pigment in the treatment of pigmented lesions.

4. A method as in claim 1, wherein the step of controlling further comprises the step of maintaining the pulse duration between a duration that is long enough to be produced by a Q-switched laser and a duration that is short enough to ensure production of a microplasma in the targeted lesion.

5. A method as in claim 1, wherein the step of controlling further comprises the step of maintaining the pulse duration between approximately 0.1 nanoseconds and approximately 100 nanoseconds.

6. A method as in claim 1, wherein the step of controlling further comprises the step of maintaining the peak irradiance between approximately $10^7$ W/cm$^2$ and approximately $10^{12}$ W/cm$^2$.

7. A method as in claim 1, wherein the step of controlling further comprises the step of maintaining the smallest dimension of the focal spot between approximately 5 micrometers and approximately 500 micrometers.

8. A method as in claim 1, wherein the step of controlling further comprises the steps of:

maintaining the peak irradiance between approximately $10^7$ W/cm$^2$ and approximately $10^{12}$ W/cm$^2$;

maintaining the pulse duration between approximately 0.1 nanoseconds and approximately 100 nanoseconds;

maintaining the smallest dimension of the focal spot between approximately 5 micrometers and approximately 500 micrometers.

9. A method as in claim 1, wherein the pulse energy of each pulse is between approximately 0.1 millijoules and approximately 100 millijoules.

10. A method as in claim 1, wherein the wavelength of each pulse has a magnitude that substantially minimizes the loss of pulse energy due to absorption and scattering by the skin tissue.

11. A method as in claim 1, wherein the wavelength of each pulse is between approximately 800 nanometers and approximately 1400 nanometers.

12. A method as in claim 1, further comprising the step of applying pressure to the target region of the skin.

13. A method as in claim 1, further comprising the step of controlling the cone angle of the beam to have a magnitude such that tissue ablation in tissue that is anterior to the target region of the skin is substantially minimized.

14. A method as in claim 1, further comprising the step of controlling the cone angle of the beam to be between approximately 5 degrees and approximately 40 degrees.

15. A method as in claim 1, further comprising the step of controlling the cone angle of the beam to be greater than 10 degrees.

16. A method as in claim 1, further comprising the step of scanning the beam to each of a plurality of locations within a treatment area of the skin such that exactly one radiation pulse is delivered to each location.

17. A method for treatment of cutaneous vascular and pigmented lesions, comprising the steps of:

generating a pulsed beam of laser radiation having a peak irradiance, pulse duration and focal spot size such that a microplasma is created in the targeted lesion of the skin; and directing the beam to a target region of the skin and scanning the beam to ensure the delivery of one pulse on each location within a treatment area.

* * * * *